United States Patent
Kanzawa et al.

(10) Patent No.: US 6,858,454 B1
(45) Date of Patent: Feb. 22, 2005

(54) METHOD FOR MEASURING SEMICONDUCTOR CONSTITUENT ELEMENT CONTENT AND METHOD FOR MANUFACTURING A SEMICONDUCTOR DEVICE

(75) Inventors: Yoshihiko Kanzawa, Yawata (JP); Tohru Saitoh, Ibaraki (JP); Takeshi Takagi, Kyoto (JP); Katsuya Nozawa, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/674,523

(22) Filed: Oct. 1, 2003

(51) Int. Cl.[7] ............................................... H01L 21/66
(52) U.S. Cl. ............................ 438/16; 438/14; 356/937
(58) Field of Search .............................. 438/14, 16, 18; 257/48; 356/937

(56) References Cited

U.S. PATENT DOCUMENTS 6,518,572 B1 * 2/2003 Kishii et al. ............ 250/339.08

2002/0106819 A1    8/2002  Nozawa et al.
2004/0014250 A1 *  1/2004  Peterson et al. .............. 438/14

* cited by examiner

Primary Examiner—Asok Kumar Sarkar
(74) Attorney, Agent, or Firm—McDermott Will & Emery LLP

(57) ABSTRACT

A method for measuring semiconductor constituent element content utilizes the steps of: obtaining a film thickness of an SiGeC layer formed on a semiconductor substrate by evaluation using spectroscopic ellipsometry; measuring infrared absorption spectrum of the SiGeC layer; and obtaining a C content of the SiGeC layer based on the film thickness and the infrared absorption spectrum of the SiGeC layer. The method: obtaining an apparent Ge content of the SiGeC layer by evaluation using spectroscopic ellipsometry; and obtaining an actual Ge content of the SiGeC layer based on the apparent Ge content and the C content. The constituent element content of the SiGeC layer can be easily and accurately measured according to the above-mentioned method.

16 Claims, 14 Drawing Sheets

Fig.11
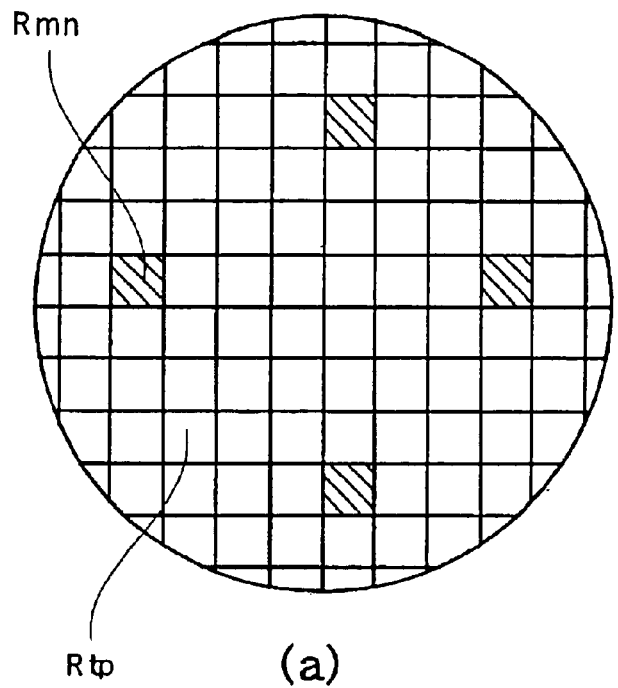
(a)
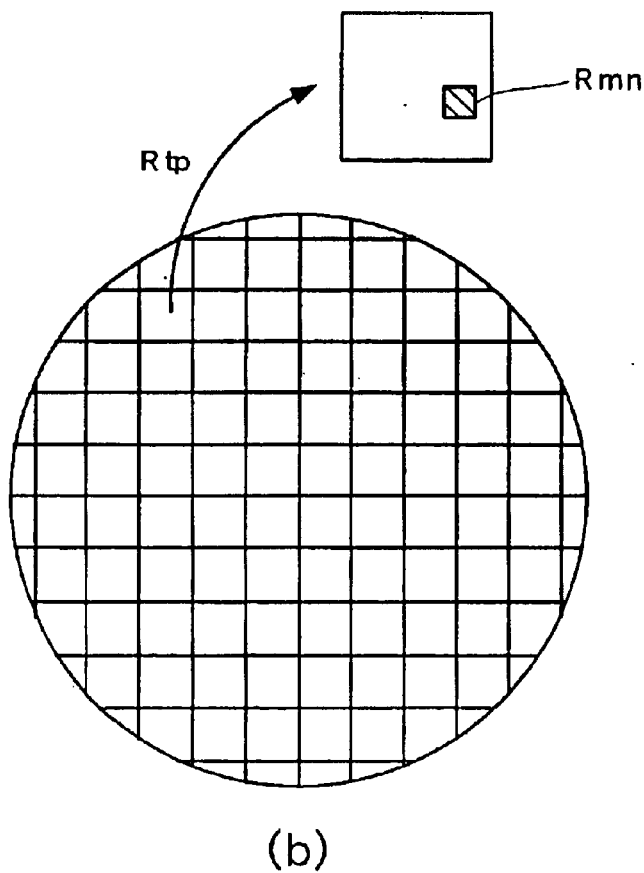
(b)

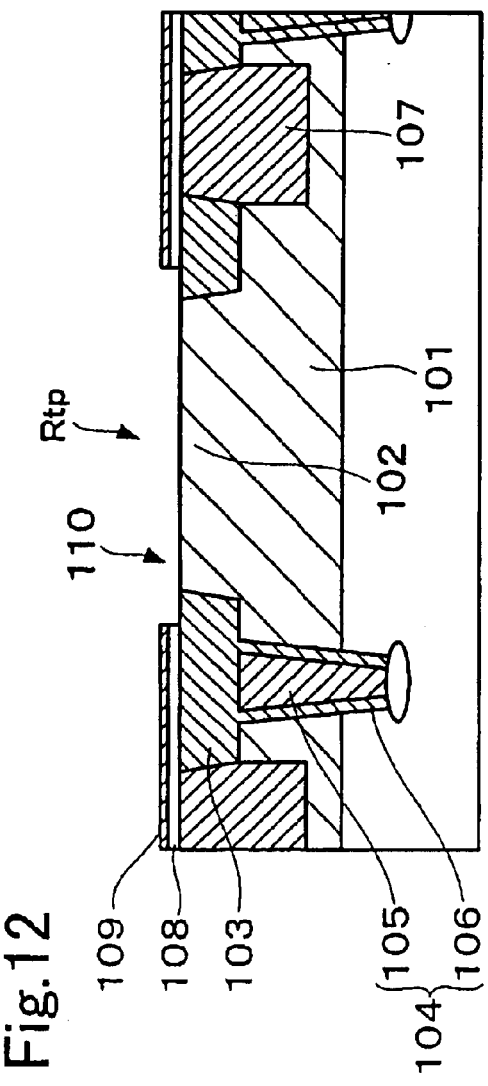
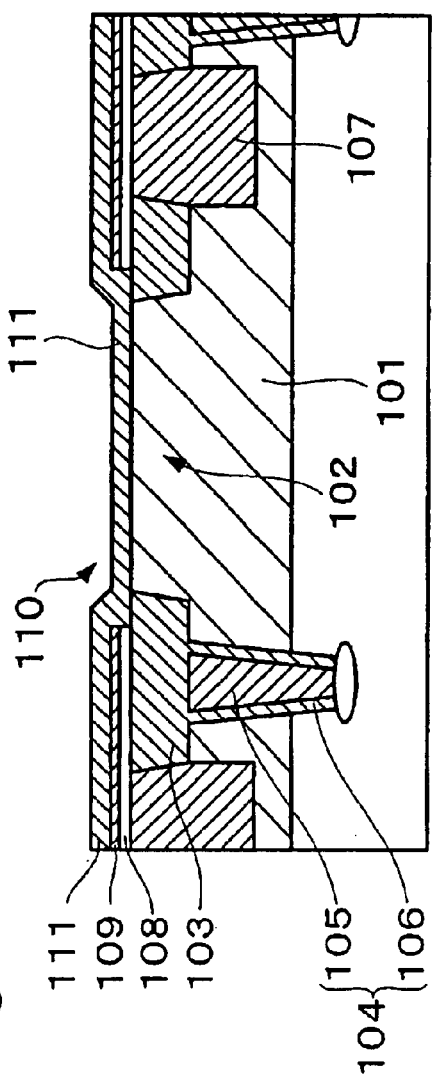

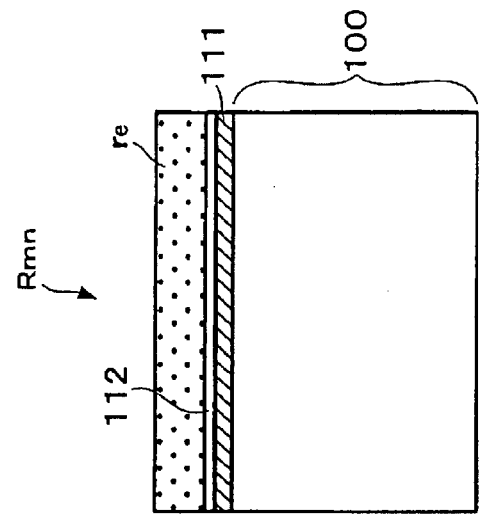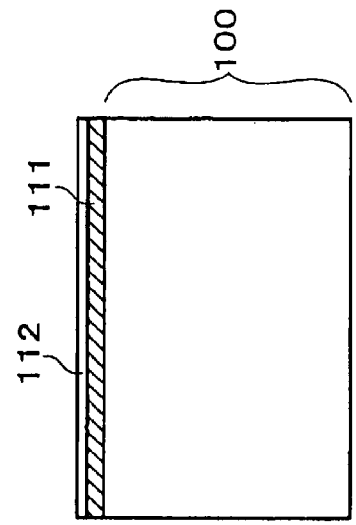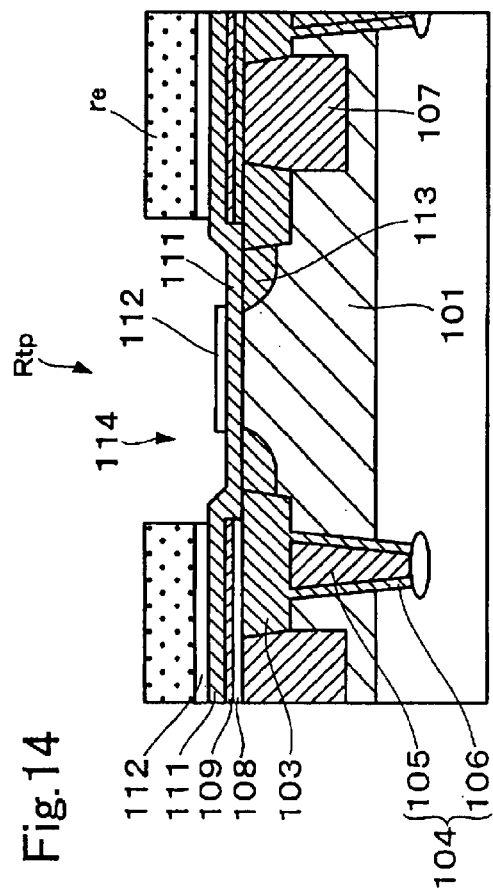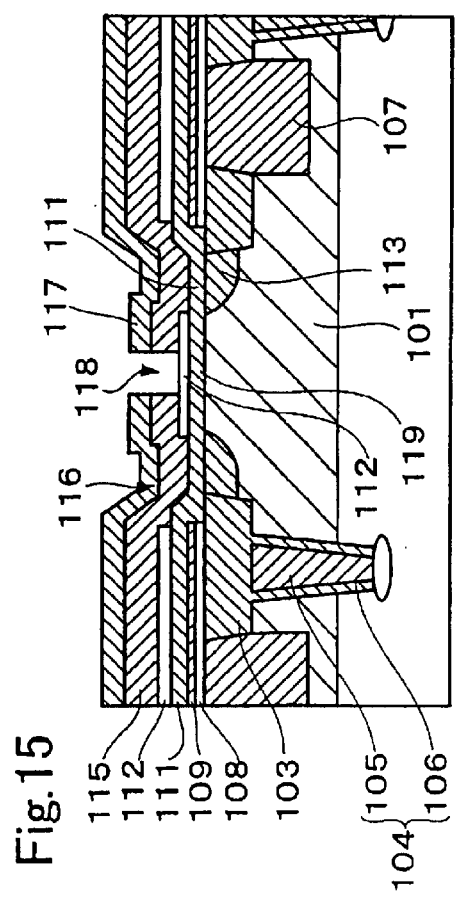

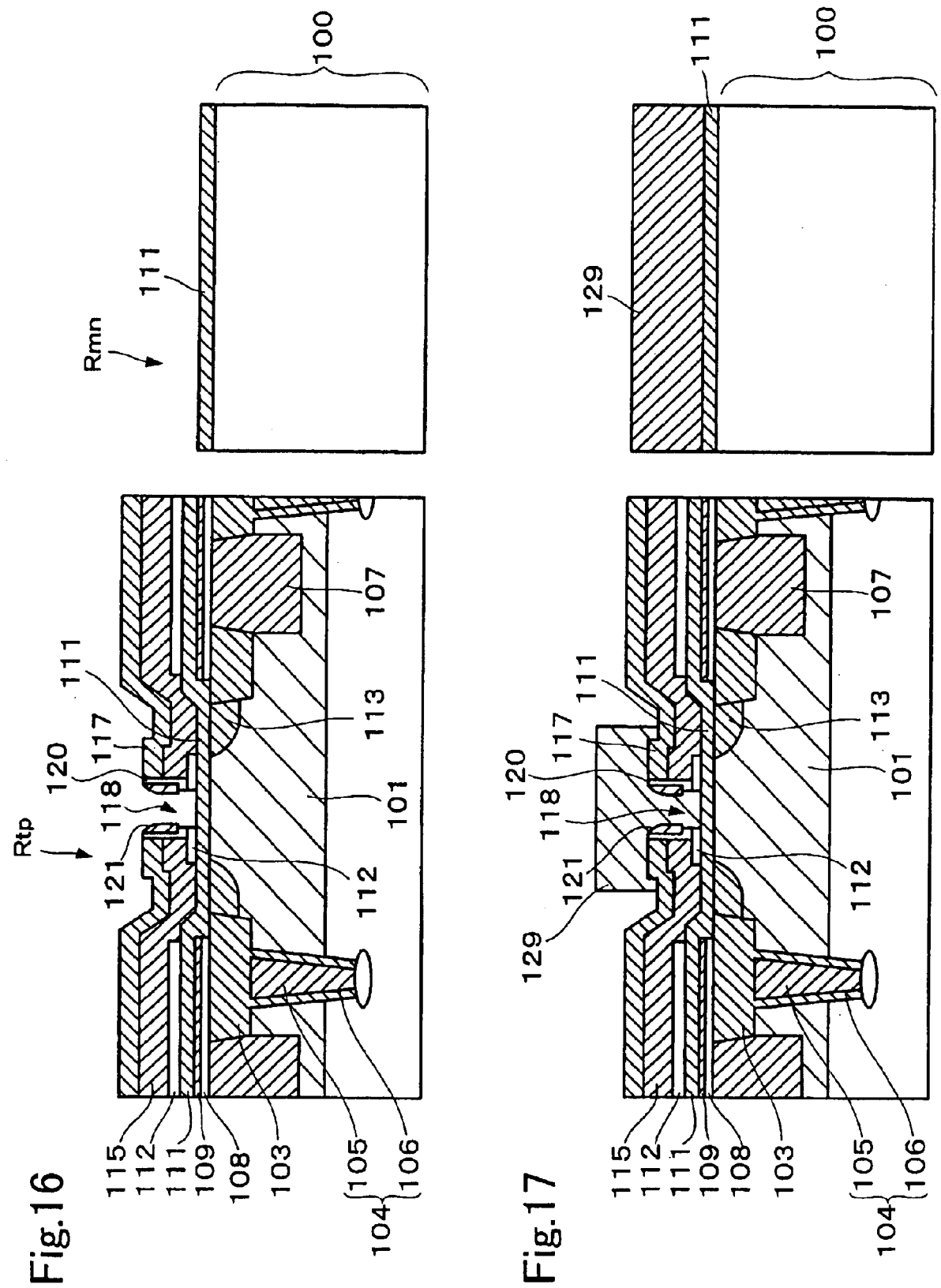

METHOD FOR MEASURING SEMICONDUCTOR CONSTITUENT ELEMENT CONTENT AND METHOD FOR MANUFACTURING A SEMICONDUCTOR DEVICE

TECHNICAL FIELD

The present invention relates to a method for measuring semiconductor constituent element content, and a method for manufacturing a semiconductor device. More specifically, the present invention relates to a method for measuring the content of the elements that constitute an SiGeC layer and a method for manufacturing a semiconductor device having an SiGeC layer.

BACKGROUND OF THE INVENTION

In recent years, transistors having an SiGe layer or an SiGeC layer have received widespread attentions because such a transistor offers potential as an MIS transistor or a bipolar transistor which can operate at high speed. When manufacturing a semiconductor device having such a semiconductor layer, the film thickness and the constituent element content (for example, Ge content in the case of an SiGe layer, and Ge and C content in the case of an SiGeC layer) of the semiconductor layer must be controlled with high precision. Thus, these values must be calculated accurately during inspection.

The spectroscopic ellipsometry method has been proposed for measuring the composition and film thickness of a thin layer formed in semiconductor processes as disclosed, for example, in United States Unexamined Patent Publication No. 2002/0106819 (published on Aug. 8, 2002, Nozawa et al., which is identical to Japanese Unexamined Patent Publication No. 2002-76083).

Known measurement methods adopting spectroscopic ellipsometry, however, still have room for improvement in measurement accuracy. This is because measurement error tends to increase when measuring the constituent element content of an SiGeC layer, particularly.

The X-ray diffraction method (XRD method), secondary ion mass spectrometry method (SIMS method), etc., are known as other methods for measuring the composition and film thickness of a semiconductor layer. These methods can measure the constituent element content with high accuracy. However, large-scale devices, such as an X-ray diffraction device and a mass spectroscope, are required, making these methods inconvenient for measuring at manufacturing sites, and thus are not practical.

DISCLOSURE OF THE INVENTION

An object of the present invention is to provide a method for measuring the semiconductor constituent element content which will enable the easy and accurate measurement of the constituent element content of an SiGeC layer. Further, an object of the present invention is to provide a method for manufacturing a semiconductor device which can enhance manufacturing yields using the method.

The objects of the present invention can be achieved by a method for measuring semiconductor constituent element content comprising the steps of: obtaining a film thickness of an SiGeC layer formed on a semiconductor substrate by evaluation using spectroscopic ellipsometry; measuring infrared absorption spectrum of the SiGeC layer; and obtaining a C content of the SiGeC layer based on the film thickness and the infrared absorption spectrum of the SiGeC layer.

The method for measuring semiconductor constituent element content is preferred to further comprise the steps of: obtaining an apparent Ge content of the SiGeC layer by evaluation using spectroscopic ellipsometry; and obtaining an actual Ge content of the SiGeC layer based on the apparent Ge content and the C content.

The objects of the present invention can be achieved by a method for manufacturing a semiconductor device comprising the steps of: establishing a chip area and a monitor area on a semiconductor substrate; forming an SiGeC layer in the chip area and the monitor area; obtaining a film thickness and an apparent Ge content of the SiGeC layer formed in the monitor area by evaluation using spectroscopic ellipsometry; measuring infrared absorption spectrum of the SiGeC layer; obtaining C content of the SiGeC layer based on the film thickness and the measured infrared absorption spectrum of the SiGeC layer; obtaining an actual Ge content of the SiGeC layer based on the apparent Ge content and the C content; and feeding back the evaluation data of the obtained C content, actual Ge content and film thickness of the SiGeC layer to growth conditions for the SiGeC layer.

BRIEF DESCRIPTION OF THE DRAWINGS

FIGS. 11(a) and (b) are plan views showing a chip area and a monitor area formed on a substrate.

FIGS. 12 through 20 are process charts for illustrating a method for manufacturing an SiGeC-HBT device.

BEST MODE FOR CARRYING OUT THE PRESENT INVENTION (Method for Measuring the Semiconductor Constituent Element Content)

Figure 1:
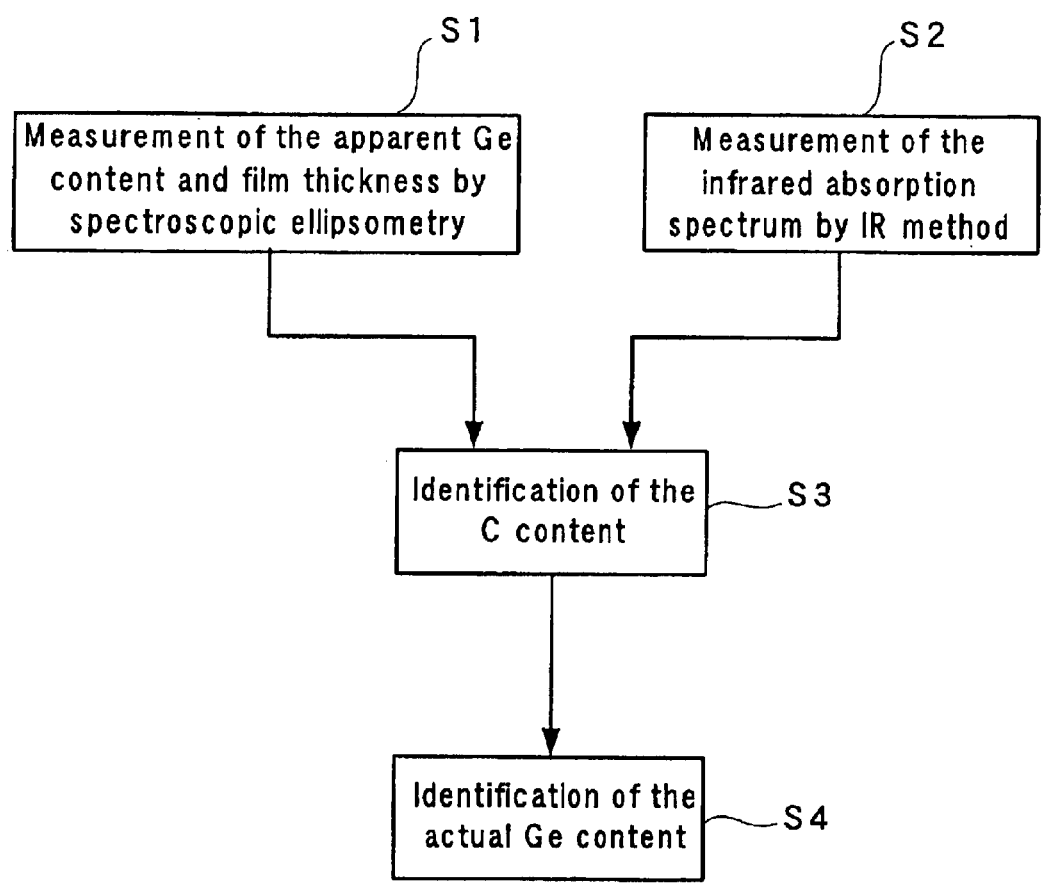
FIG. 1 is a flow chart illustrating a method for measuring the semiconductor constituent element content according to one embodiment of the present invention.

Hereinafter, embodiments of the present invention will be described with reference to drawings. FIG. 1 is a flow chart illustrating a method for measuring semiconductor constituent element content according to one embodiment of the present invention. The present embodiment employs spectroscopic ellipsometry as the measurement method so as to calculate the apparent Ge content and film thickness of an SiGeC layer formed on a semiconductor substrate (Step 1).

Spectroscopic ellipsometry is used to obtain information about a measurement sample by irradiating the sample with linearly polarized light, and measuring the change in the polarization states of the reflected light. The linearly polarized light has a P polarization component in which an electric-field vector is in parallel to the plane of incidence and an S polarization component in which an electric-field vector is perpendicular to the plane of incidence. When each complex reflection coefficient thereof is set to Rp and Rs, respectively, ρ=Rp/Rs becomes a complex number and is expressed by the following formula using the two real numbers, Ψ and Δ.

$$\rho = Rp/Rs = \tan \Psi e^{i\Delta} \text{ (i is an imaginary unit)} \quad (1)$$

Figure 2:
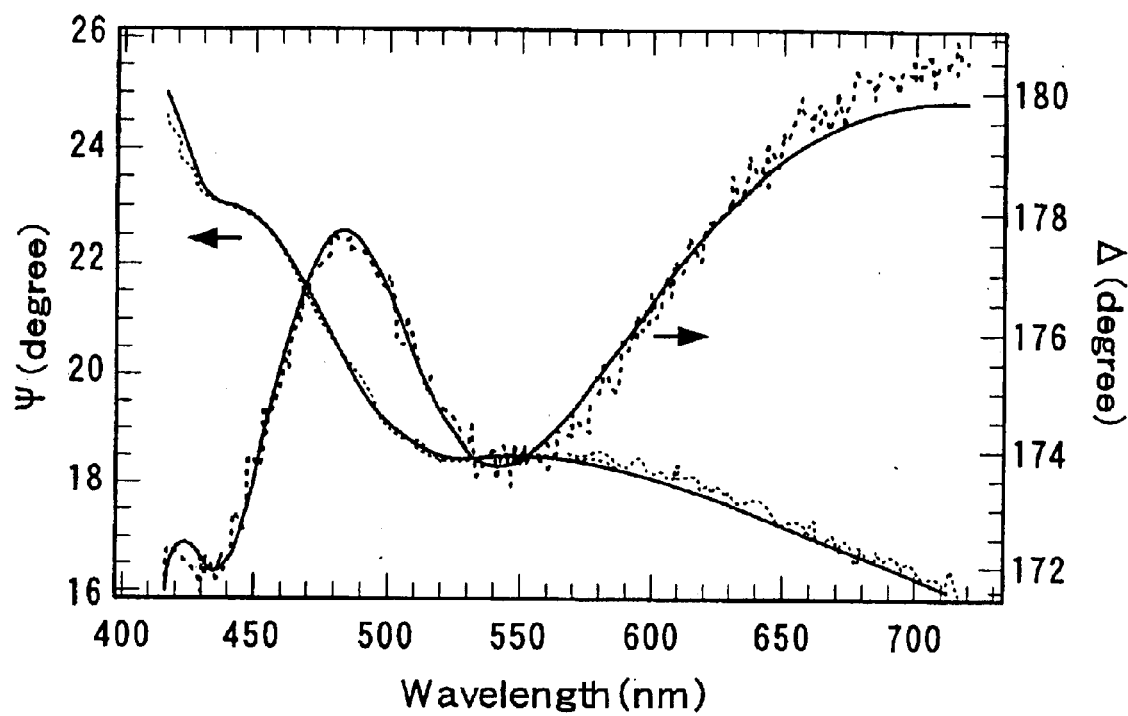
FIG. 2 shows the measurement results of the spectra shapes of $\Psi$ and $\Delta$ for an SiGeC layer measured by spectroscopic ellipsometry.

Spectroscopic ellipsometry obtains spectra by measuring the Ψ and Δ of the light of each wavelength. FIG. 2 shows a measurement result example of spectra shapes of the Ψ and Δ for the SiGeC layer by using the spectroscopic ellipsometry at the incident angle of 65°.

The apparent Ge content and the film thickness of an SiGeC layer can be calculated by fitting the obtained Ψ and Δ to a reference model (analysis model). The settings of the reference model can be determined by referring to United States Unexamined Patent Publication No. 2002/0106819 (published on Aug. 8, 2002, Nozawa et al., which is identical to Japanese Unexamined Patent Publication No. 2002-76083). In more detail, a reference model is obtained by preparing some samples, whose composition and film thickness are known, as a reference, and measuring the ellipsometric spectra of these samples to serve as a reference. The ellipsometric spectra whose composition and the like are unknown are matched with (i.e., fitting) the spectra serving as a reference, so as to clarify the composition thereof.

It is impossible to prepare reference samples which cover all types of composition and film thickness for measuring ellipsometry spectra whose composition and the like are unknown. Thus, in practice, fitting is carried out by interpolating the spectra of some the reference samples.

Figure 3:
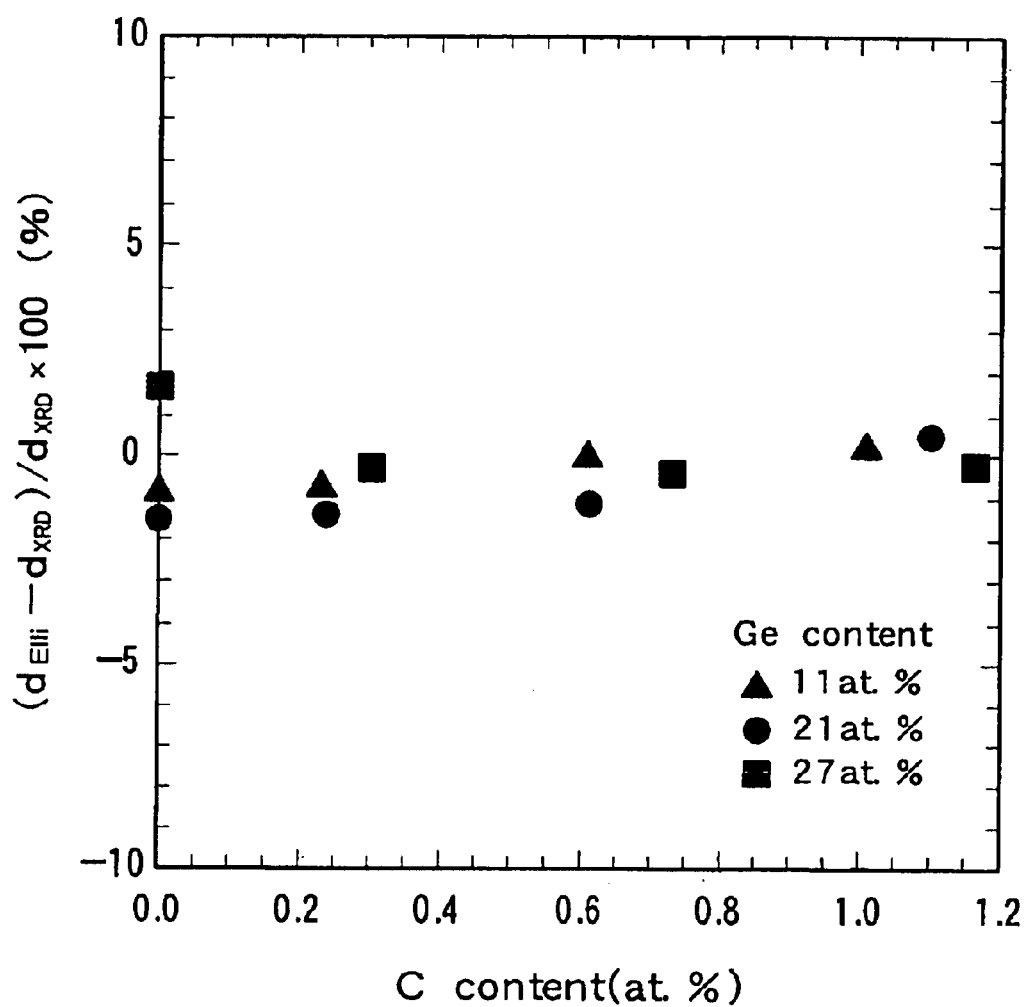
FIG. 3 shows the dependence of the film thickness deviation on the C content.

Experiments conducted by the inventors show that the reference model for an SiGe layer can be used to measure the film thickness of an SiGeC layer by using spectroscopic ellipsometry. FIG. 3 shows the dependence of the deviation on the C content. In FIG. 3, the ordinate axis plots the deviation between the film thickness of an SiGeC layer obtained by spectroscopic ellipsometry using a reference model for an SiGe layer and the film thickness of the SiGeC layer obtained by the XRD method, and the abscissa axis plots the C content of the SiGeC layer. The deviation in the specification signifies the value which is obtained by dividing the difference between the film thickness $d_{Elli}$ obtained by spectroscopic ellipsometry and the film thickness $d_{XRD}$ obtained by the XRD method by the film thickness $d_{XRD}$ (($d_{Elli} - d_{XRD})/d_{XRD}$)).

As shown in the figure, the deviation is within the range of ±2% in all of the cases of Ge content of 11%, 21% and 27%. It means that highly accurate measurement results are obtained by using the reference model for an SiGe layer. In other words, the inventors have shown that the reference model for an SiGe layer can be used to measure the film thickness of an SiGeC layer by using spectroscopic ellipsometry.

The infrared absorption spectrum of an SiGeC layer can also be measured while conducting the above-mentioned Step S1 (Step S2). Step S2 may be performed either before or after Step S1. The infrared absorption spectrum of an SiGeC layer can be obtained, for example, by infrared absorption spectrometry (hereinafter, referred to as the "IR method"). The IR method measures the infrared absorption coefficient based on the intensity of infrared radiation that is transmitted through a semiconductor substrate.

Figure 4:
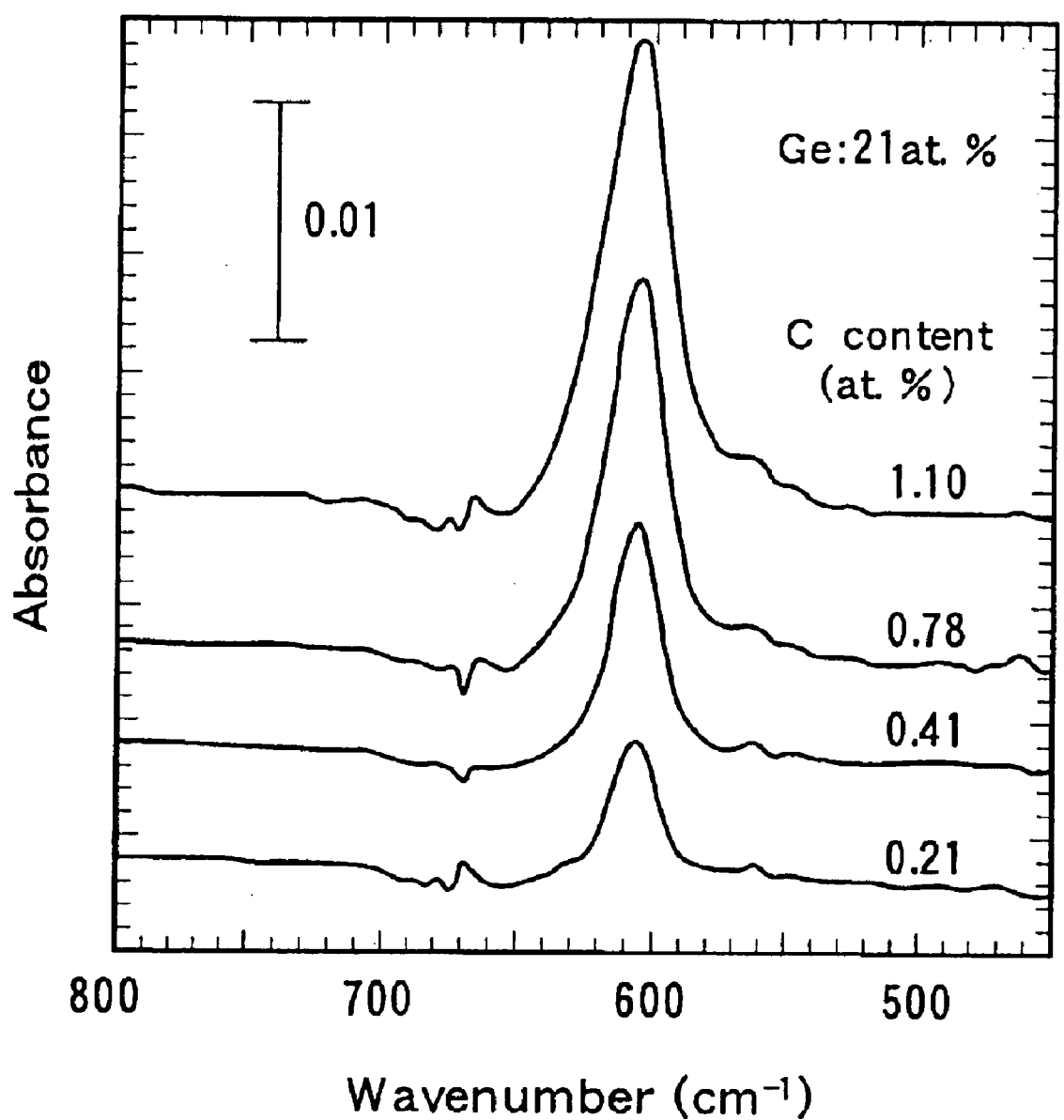
FIG. 4 shows an example of the infrared absorption spectrum obtained by the IR method.

An example of the infrared absorption spectrum obtained by the IR method is shown in FIG. 4. FIG. 4 shows the infrared absorption spectra of substrates having SiGeC layers with various levels of C content. The substrates were 8 inches in size and about 720 μm thick. The SiGeC layers were formed to have a 150 nm thickness and 21% Ge content. The infrared absorption spectrum was then measured in SiGeC layers with C content of 0.21%, 0.41%, 0.78% and 1.10%. The constituent element content (C content or Ge content) and the film thickness of the SiGeC layers were determined by the XRD method.

Figure 5:
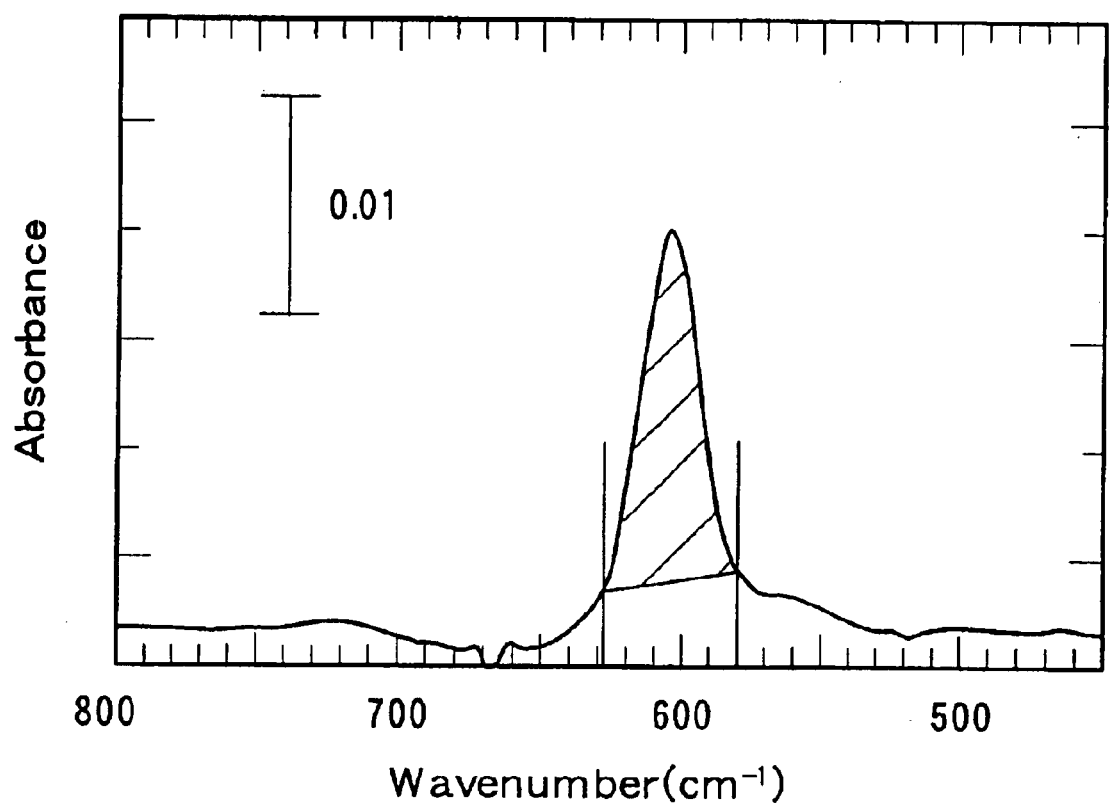
FIG. 5 shows an example of a method for specifying the spectrum peak portion.

As shown in FIG. 4, each of the infrared absorption spectra reaches a peak at the wavenumber of about 600 (cm$^{-1}$). The integrated intensity at the peak portion (peak area) increases with an increase in the C content. The method for specifying the peak portion is not particularly limited, but vertical segmentation can be employed, for example. As shown in FIG. 5, the shaded area in the figure is defined as the integrated intensity of the peak portion which is cut by a straight line by using the vertical segmentation, in which two vertical lines are placed on either side of the peak portion at a predetermined interval and the straight line is drawn to connect the points where these vertical lines intersect the infrared absorption spectrum.

Figure 6:
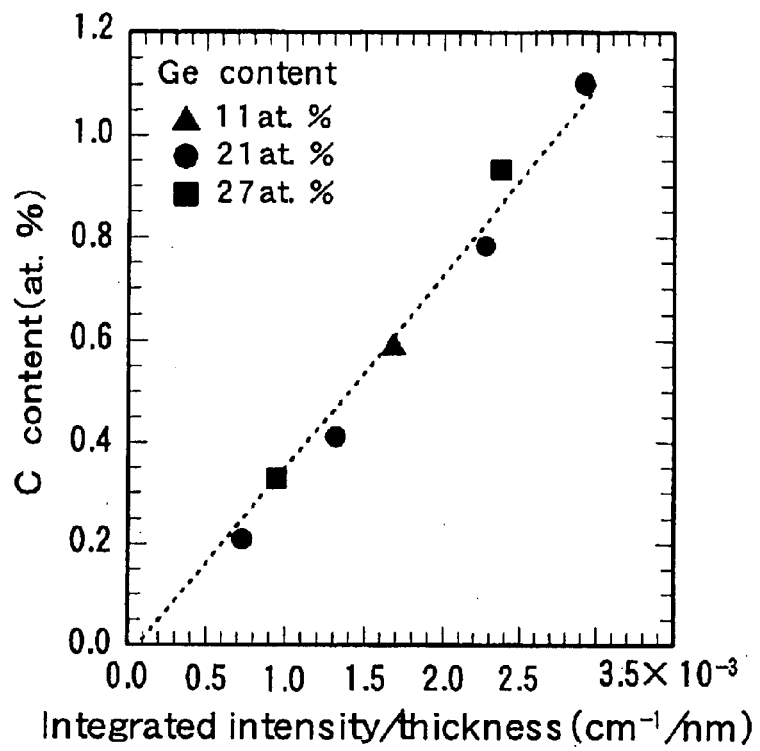
FIG. 6 shows the relation between unit integrated intensity and the C content of an SiGeC layer.

FIG. 6 shows the relation between the unit integrated intensity and the C content of an SiGeC layer. The unit integrated intensity is a value obtained by normalizing the integrated intensity at the peak portion of the infrared absorption spectrum by the film thickness of the SiGeC layer, and more specifically, is the value obtained by dividing the integrated intensity at the peak portion of the infrared absorption spectrum by the film thickness of the SiGeC layer. As shown in the figure, the C content increases linearly with an increase in the unit integrated intensity regardless of the Ge content, with little variation seen. SiGeC layers with various film thicknesses were measured in the same manner, and almost the same results were obtained as in FIG. 6. Thus, the inventors have shown that a linear relationship exists between the unit integrated intensity and the C content of the SiGeC layer.

Figure 7:
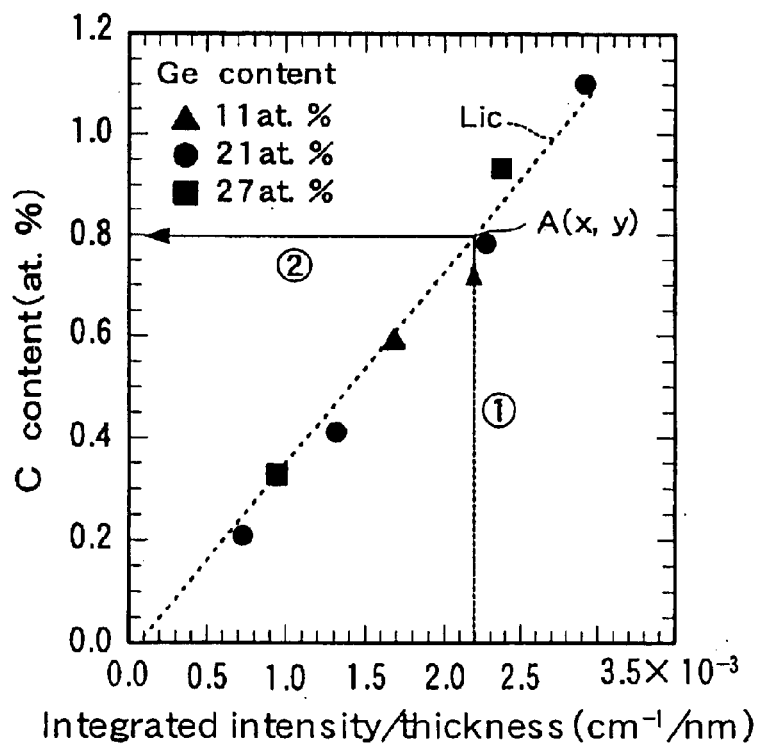
FIG. 7 shows a method for obtaining the C content of an SiGeC layer.

Next, the C content of the SiGeC layers was identified (Step 3) using the measurement results obtained by Steps S1 and S2. More specifically, the film thickness of the SiGeC layer is obtained in Step S1, and the infrared absorption spectrum of the SiGeC layer is obtained in Step S2. Thus, the integrated intensity at the peak portion of the infrared absorption spectrum is normalized by the film thickness, whereby the unit integrated intensity can be obtained. The C content of the SiGeC layer can be obtained based on the unit integrated intensity thus obtained, referring to the graph shown in FIG. 7. For example, when the unit integrated intensity is 2.2×10$^{-3}$ (cm$^{-1}$/nm), as shown in FIG. 7, point A (coordinates x, y) on the correlated straight line $L_{ic}$ is obtained from arrow line ①, and thus the C content of the SiGeC layer can be obtained as 0.8 at. % along the arrow line ②.

Figure 8:
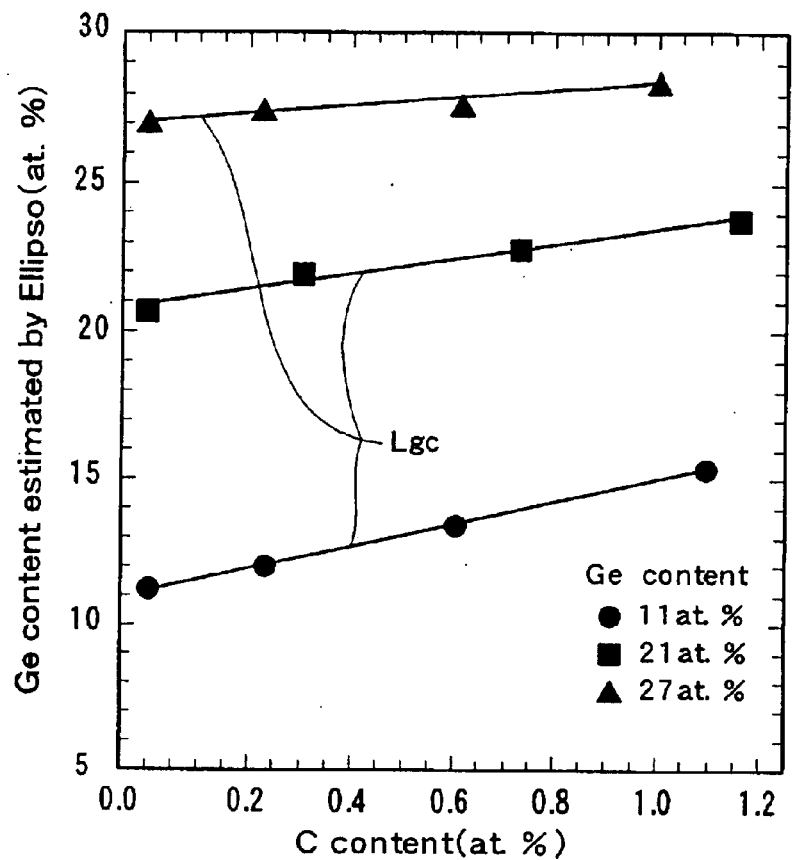
FIG. 8 shows the relation between the apparent Ge content of an SiGeC layer and the C content of an SiGeC layer.

The C content of the SiGeC layer is thus obtained as described above. Thereafter, the actual Ge content of the SiGeC layer is obtained (Step 4) based on the C content and the apparent Ge content of the SiGeC layer obtained in Step S1. FIG. 8 shows the relation between the apparent Ge content and the C content of an SiGeC layer based on the results of an experiment conducted by the inventors. In the specification, the apparent Ge content of an SiGeC layer is a value obtained using the reference model for the SiGeC layer. The constituent element content of an SiGeC layer (C content and Ge content) is the value measured by the XRD method.

Figure 9:
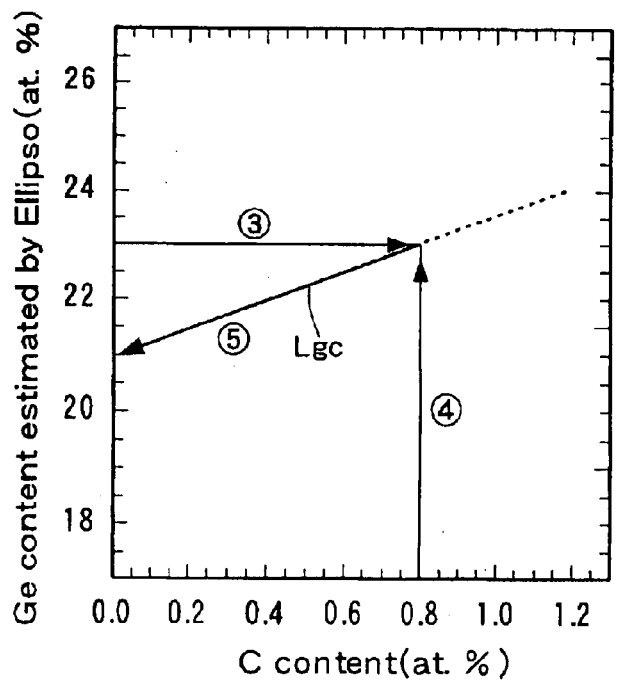
FIG. 9 shows a method for obtaining the actual Ge content of an SiGeC layer.

As shown in FIG. 8, the apparent Ge content of an SiGeC layer increases linearly with an increase in the C content. The rate of increase clearly becomes larger as the Ge content becomes smaller. Accordingly, the actual Ge content can be obtained by referring to the graph in FIG. 8 when the apparent Ge content and C content are obtained. For example, when the apparent Ge content is 23 at. % and the C content is 0.8 at. %, the actual Ge content of the SiGeC layer can be obtained as 21 at. % by specifying the correlated straight line $L_{gc}$ which intersects arrow line ③ and arrow line ④ in FIG. 9, and then obtaining the intercept of the correlated straight line $L_{gc}$ (obtaining the Ge content when the C content becomes 0 by moving in the direction of arrow line ⑤).

The actual Ge content of an SiGeC layer can also be obtained by a mathematical expression as shown below. In other words, setting the apparent Ge content to "b'", the C content to "c", and the slope of the correlated straight line to "a", the actual Ge content "b" is expressed by the following formula.

$$b = b' - a \times c \quad (2)$$

Figure 10:
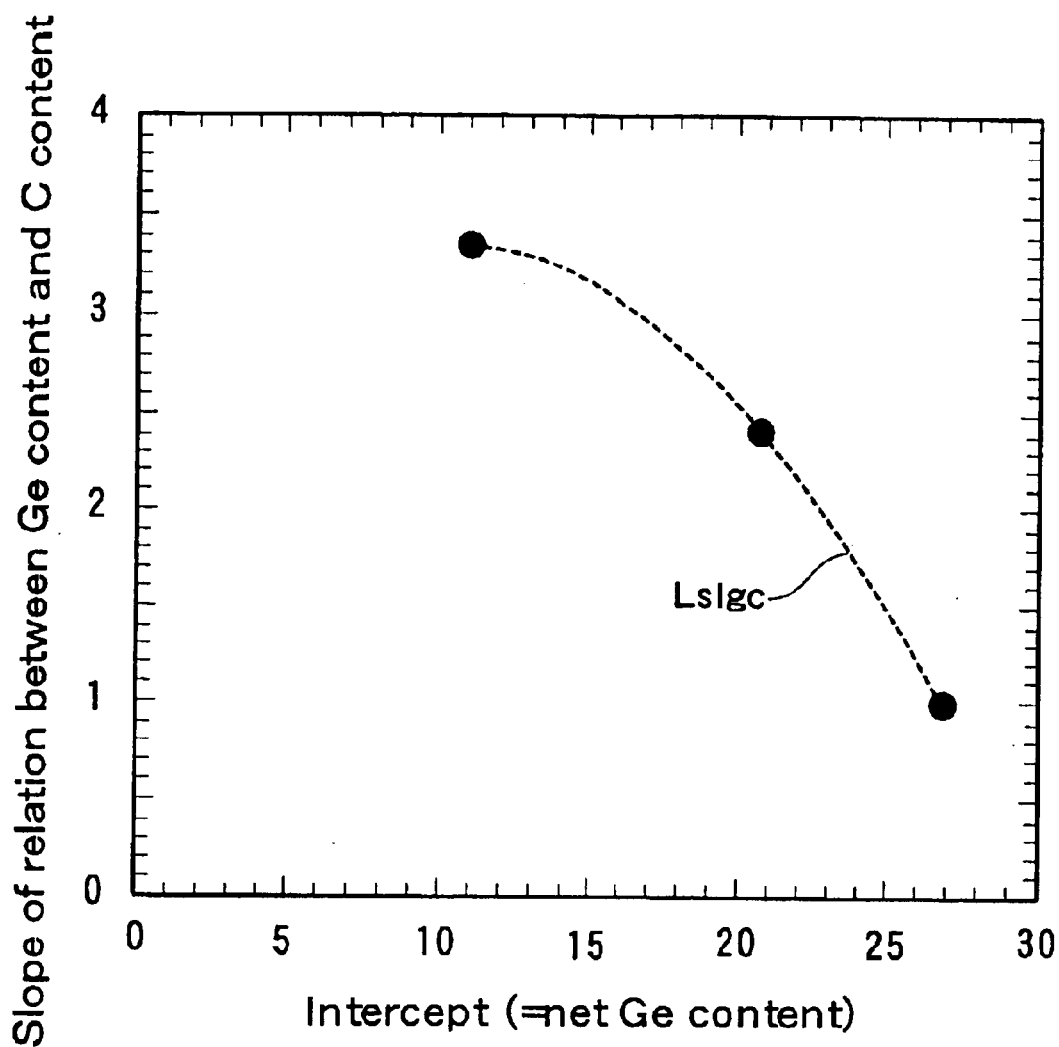
FIG. 10 shows the relation between the slope of a linear correlation and the actual Ge content.

As described above, the slope of the correlated straight line $L_{gc}$ becomes sharper as the Ge content of the SiGeC layer becomes smaller. Thus, the value of the slope of the correlated straight line "a" in formula (2) varies depending on the value of the actual Ge content "b". The relation between the two factors can be approximated to a curve, as shown in FIG. 10, by obtaining a plurality of correlated straight line varying in Ge content, as shown in FIG. 8. The approximation becomes more accurate as the number of the correlated straight line increases. For example, when the relation between the slope of the correlated straight line "a" and the actual Ge content "b" is approximated to the quadratic curve $L_{sIgc}$ the approximated relation is shown in the following formula (3):

$$a = 2.35 + 0.19b - 0.0088b^2 \quad (3)$$

When formula (3) is substituted into the above-mentioned formula (2), the actual Ge content "b" is expressed by the following formula (4):

$$b = [0.19c + 1 - \sqrt{(0.1188c^2 + (0.38 - 0.0352b') \, c + 1)}]/0.0176c \quad (4)$$

Thus, the actual Ge content "b" can be obtained based on the apparent Ge content "b'" and the C content "c" by using the above-mentioned formula (4).

As described above, the method for measuring the semiconductor constituent element content according to the present embodiment makes it possible to easily and accurately measure the constituent element content and the film thickness of an SiGeC layer while requiring neither large-scale equipment nor extensive measurements such as those, which are required by the XRD method and the SIMS method and performed mainly in a laboratory. Therefore, for example, the measurement method of the present invention can be used suitably for production control at a manufacturing site.

(Method for Manufacturing a Semiconductor Device)

Next, an embodiment that applies the above-described method for measuring semiconductor constituent element content to a method for manufacturing a semiconductor device will be described. Measuring the semiconductor constituent element content requires a monitor area for detecting the composition and film thickness of the SiGeC layer in addition to a chip area that functions as a semiconductor chip. For example, as shown in FIG. 11(a), some areas (for example, 4 areas) among a plurality of areas formed by dividing a substrate after it is manufactured are allocated as monitor areas $R_{mn}$ and the remaining are allocated as chip areas $R_{tp}$. Thus, each of a plurality of areas formed by dividing the substrate after it is manufactured can be individually allocated as a monitor area $R_{mn}$ or a chip area $R_{tp}$. Otherwise, as shown in FIG. 11(b), all areas can be defined as chip areas $R_{tp}$, and monitor areas $R_{mn}$ can be then formed on a part of each chip area. Thus, a monitor area $R_{mn}$ and chip area $R_{tp}$ can coexist in any of a plurality of areas formed by dividing a substrate after manufactured. Hereinafter, a method for manufacturing a semiconductor device employing the substrate shown in FIG. 11(a) will be described. It should be noted that a semiconductor device employing the substrate shown in FIG. 11(b) can be manufactured in the same manner.

FIGS. 12 through 20 show the processes of a method for manufacturing an SiGeC-HBT (heterojunction bipolar transistor) device. In the process shown in FIG. 12, an N-type retrograde well 101 with a depth of about 1 μm is formed at the chip area $R_{tp}$ by epitaxially growing an Si single crystal layer on the upper part of an Si substrate 100 with a primary surface (001) while doping with N-type impurities, or by injecting ions at high energy after an Si single crystal layer was epitaxially grown. The retrograde well 101 can also be formed by employing ion injection to a part of the Si substrate 100 without epitaxial growth. To yield an HBT collection layer in the area around the Si substrate 100 surface of the chip area $R_{tp}$, the N-type impurity concentration is set to about $1 \times 10^{17}$ atoms·cm$^{-3}$. On the other hand, the monitor area $R_{mn}$ is covered by a mask to prevent the injection of impurities.

Next, to separate devices, a shallow trench 103 in which silicon oxide is embedded and a deep trench 104 consisting of an undoped polysilicon film 105 surrounded by a silicon dioxide film 106 are formed in the chip area $R_{tp}$. The depths of the trenches 103 and 104 are about 0.35 μm and 2 μm, respectively. The area sandwiched by two adjacent shallow trenches 103 serves as a collector layer 102 in the Si substrate 100. An N$^+$ collector leading layer 107 for contacting the collector electrode is also formed in the area isolated from the collector area 102 by the shallow trench 103 in the Si substrate 100. In this process, there is no need to form a shallow trench at the monitor area $R_{mn}$.

Subsequently, a first oxide deposition film 108 with a thickness of about 30 nm is formed on the substrate using chemical vapor deposition (CVD) using tetra ethoxy silane (TEOS) and oxygen at a processing temperature of 680° C., followed by the formation of a polysilicon layer 109 with a thickness of about 50 nm. Then, after patterning the polysilicon layer 109 by dry etching or the like, the first oxide deposition film 108 is removed by wet etching using hydrofluoric acid, etc., and a collector aperture 110 is formed on the first oxide deposition film 108 and polysilicon layer 109 of the chip area $R_{tp}$.

At this time, the first oxide deposition film 108 and polysilicon layer 109 are also formed on the monitor area Rn, but they are completely removed from the monitor area $R_{mn}$, when forming the collector aperture 110.

Next, using the process shown in FIG. 13, the part of the chip area $R_{tp}$ that is exposed via the collector aperture 110 and the part of the monitor area $R_{mn}$ that is exposed are processed with a mixture of ammonia water and hydrogen peroxide solution to form a protective oxide film with a thickness of about 1 nm, and the substrate is inserted into the chamber of a UHV-CVD device. After the substrate is inserted, the protective oxide film is removed by heat treatment in a hydrogen atmosphere, a disilane (Si$_2$H$_6$) and germane (GeH$_4$) gas containing diborane (B$_2$H$_6$) and methyl silane (10% SiH$_3$CH$_3$/H$_2$) for doping are introduced into the chamber while heating to 550° C., so as to epitaxlially grow an SiGeC layer with a thickness of about 60 nm onto the entire surface, including the exposed parts via the collector aperture 110. Thereafter, the gas supplied successively to the chamber is replaced by disilane, and thus an Si layer with a thickness of 10 mm is epitaxially grown onto the SiGeC layer surface. The resulting SiGeC layer and Si layer constitute an Si/SiGeC layer 111 on the substrate surface. Here, boron (B) is introduced to the SiGeC layer, making it a P-type layer.

Next, the composition and film thickness of the SiGeC layer in the Si/SiGeC layer 111 in the monitor area R$_{mn}$ are measured by the spectroscopic ellipsometry and the IR method mentioned in the above for measuring the semiconductor constituent element content. An Si layer (an Si cap layer) is formed on the SiGeC layer surface, but there is no possibility that the Si layer will affect the accuracy of measuring the composition and film thickness of the SiGeC layer.

The evaluation data of the composition and film thickness of an SiGeC layer thus obtained for each monitor area R$_{mn}$ can be fed back to the growth conditions for forming a subsequent SiGeC layer. For example, if the mean value or variation in the evaluation data for each monitor area R$_{mn}$ deviates from the preset reference value by a predetermined amount (for example, ±10%), the process can be temporarily interrupted so as to analyze the evaluation data, and then revise the growth conditions of the Si/SiGeC layer 111 accordingly. The evaluation data may also be analyzed by considering the distribution of evaluation data for multiple monitor areas R$_{mn}$ set within the substrate surface.

Subsequently, a second oxide deposition film 112 with a film thickness of 30 nm is formed on the substrate to serve as an etching stopper by the process shown in FIG. 14. The chip area R$_{tp}$ of the second oxide deposition film 112 is then patterned by dry etching using a resist mask re, to form a base junction aperture 114. Consequently, the Si/SiGeC layer 111 is exposed via the base junction aperture 114 while the central portion of the Si/SiGec layer 111 is covered with the second oxide deposition film 112. At this time, the resist mask r$_e$ remains on the second oxide deposition film 112 of the monitor area R$_{mn}$.

The resist mask r$_e$ that has been formed is used to inject P-type impurities such as boron (B) into the chip area R$_{tp}$ so as to form a junction leak prevention layer 113 having a concentration of about 3×10$^{17}$ atoms·cm$^{-3}$ in the vicinity of the surface area.

The resist mask r$_e$ is then removed, and, employing the process shown in FIG. 15, the CVD method is used to deposit a P$^+$, polysilicon layer 115 to a thickness of about 150 nm that is doped to a high concentration of 1×10$^{20}$ atoms·cm$^{-3}$ or more onto the substrate. Subsequently, a third oxide deposition film 117 with a thickness of about 100 nm is deposited. Dry etching is then used to pattern the third oxide deposition film 117 and the P+ polysilicon layer 115 in the chip area R$_{tp}$ so as to form a base aperture 118, which extends to the second oxide deposition film 112, in the third oxide deposition film 117 and the P+ polysilicon layer 115. The base aperture 118 has an aperture area that is smaller than the area of the second oxide deposition film 112 which exists on the base junction aperture 114 so that none of the second oxide deposition film 112 is exposed. The third oxide deposition film 117 and the P$^+$ polysilicon layer 115 of the monitor area R$_{mn}$ are removed when forming the base aperture 118. This process results in the formation of an external base 116 composed of the P$^+$ polysilicon layer 115, etc. On the other hand, an internal base 119 is formed under the location in which the Si/SiGeC layer 111 is exposed via the base aperture 118.

Next, employing the process shown in FIG. 16, a fourth oxide deposition film 120 with a thickness of about 30 nm and a polysilicon film with a thickness of about 150 nm are deposited onto the entire substrate surface using the CVD method. The polysilicon film is then etched back by anisotropic dry etching to form polysilicon sidewalls 121 on the sides of the P$^+$ polysilicon layer 115 and the third oxide deposition film 117 in the chip area R$_{tp}$, as sandwiching the fourth oxide deposition film 120. At this time, the fourth oxide deposition film 120 and the polysilicon film in the monitor area R$_{mn}$ are all removed.

Subsequently, wet etching employing hydrofluoric acid or the like is used to remove the exposed areas of the second oxide deposition film 112 and the fourth oxide deposition film 120 in the chip area R$_{tp}$. Thus, the Si layer on the top of the Si/SiGeC layer 111 is exposed via the base aperture 118. The wet etching is isotropic, so the second oxide deposition film 112 and the fourth oxide deposition film 120 are etched also in a transverse direction, which increases the size of the base aperture 118. More specifically, the base aperture width is determined by the wet etching quantity used in this process. However, the surfaces of the parts of the Si substrate 100 that are covered by the P$^+$ polysilicon layer 115, such as the N$^+$ collector leading layer 107, are not exposed. At this time, the second oxide deposition film 112 is also removed in the monitor area R$_{mn}$ in the same manner as in the above-mentioned process for exposing the Si/SiGeC layer 111 by wet etching.

Using the process shown in FIG. 17, an N$^+$ polysilicon layer 129 with a thickness of about 250 nm is formed on the substrate, then dry etching is used to pattern the N$^+$ polysilicon layer 129 and the third oxidation deposition film 117, thereby forming an emitter lead electrode in the chip area R$_{tp}$. At this time, the N$^+$ polysilicon layer 129 is left remaining in the monitor area R$_{mn}$.

Figure 18:
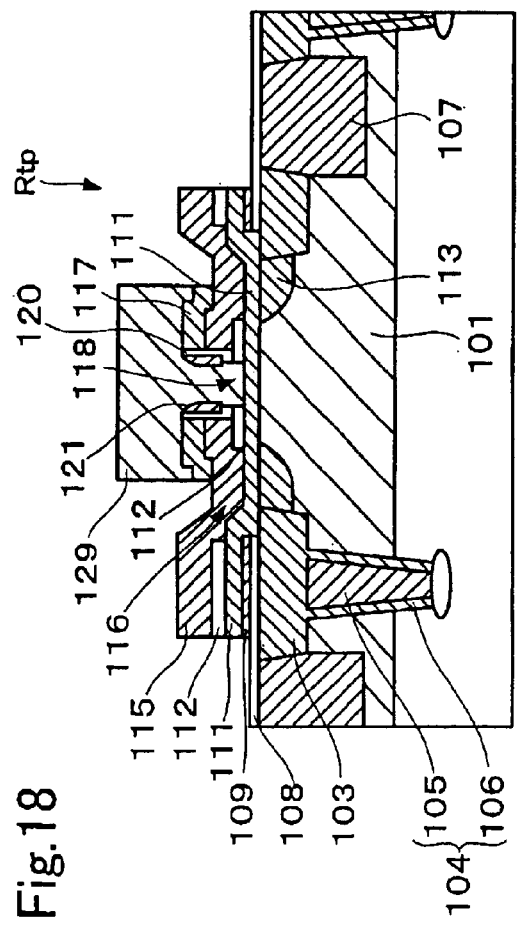

Using the process shown in FIG. 18, dry etching is used to pattern the P$^+$ polysilicon layer 115, the second oxide deposition film 112, the Si/SiGeC layer 111 and the polysilicon layer 109, to determine the shape of the external base 116.

Figure 19:
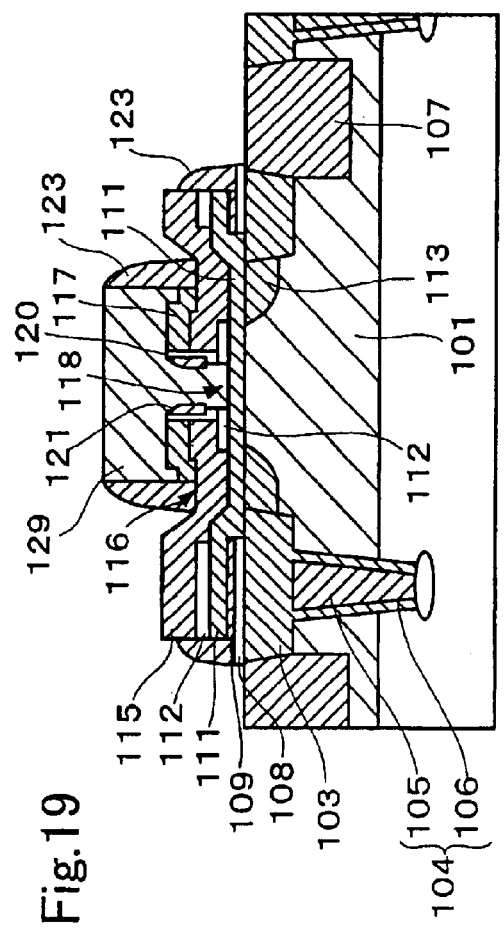

Next, using the process shown in FIG. 19, an oxide deposition film with a thickness of about 120 nm is formed on the substrate, then dry etching is used to form sidewalls 123 at the sides of the N$^+$ polysilicon layer 129 and the P$^+$ polysilicon layer 115 in the chip area R$_{tp}$. This dry etching (over etching) also removes the exposed part of the first oxide deposition film 108, thereby exposing the surface of the N$^+$ polysilicon layer 129 and the P$^+$ polysilicon layer 115 as well as the N$^+$ collector leading layer 107 in the chip area R$_{tp}$.

Figure 20:
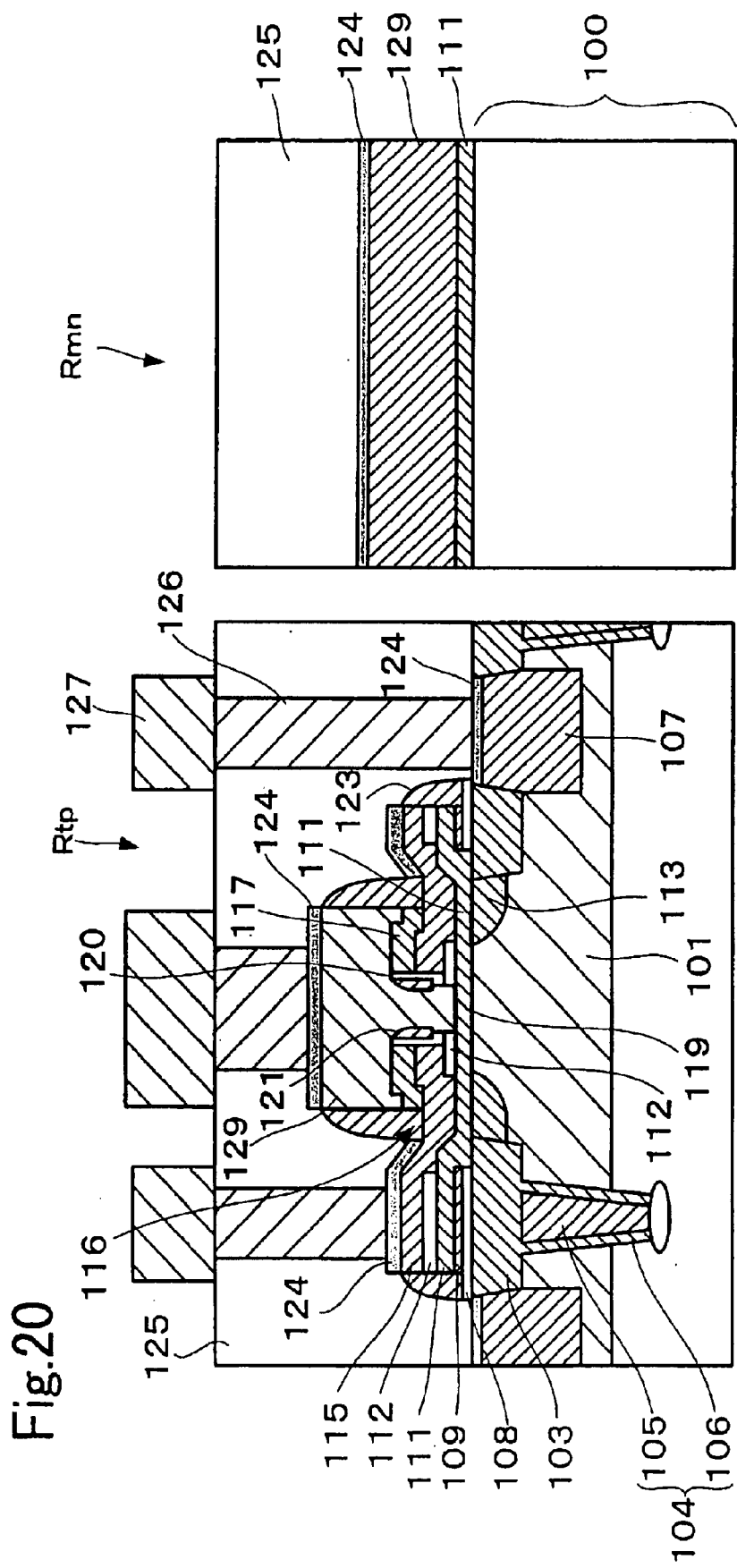

Further, using the process shown in FIG. 20, sputtering is used to deposit Ti film with a thickness of about 40 nm onto the entire surface of the substrate, then RTA (rapid thermal annealling) is conducted at 675° C. for 30 seconds, to form Ti silicide layers 124 on each of the exposed surfaces of the N$^+$ polysilicon layer 129, the P$^+$ polysilicon layer 115 and the N$^+$ collector leading layer 107. Only the unreacted area of the Ti layer is then selectively removed, after which the Ti silicide layer 124 is annealed to change its crystal structure.

Subsequently, an interlayer dielectric 125 is formed on the entire substrate surface. A plurality of contact holes are formed which pass through the interlayer dielectric 125 to reach each of the Ti silicide layers 124 formed on the N+ polysilicon layer 129, the P+ polysilicon layer 115 and the N+collector leading layer 107. W films are embedded in each contact hole to form W plugs 126. Thereafter, aluminium alloy film is deposited on the entire surface of the substrate and then patterned to form a metal wiring 127 which is connected to each of the W plugs and extends along the surface of the interlayer dielectric 125. It is not necessary to form the contact holes and the metal wiring in the monitor area $R_{mn}$.

An HBT (heterojunction bipolar transistor) with a collector composed of N type Si, a base composed of P+ type SiGeC, and an emitter composed of N+ type Si is formed by the above-mentioned process. Here, the Si layer of the Si/SiGeC layer 111 in the chip area $R_{tp}$ is an N+ type Si layer because high-concentration N type impurities (phosphorus etc.) are dispersed from the N+ polysilicon layer 129.

Using the above-mentioned method for manufacturing a semiconductor device, the substrate provided with the monitor area $R_{mn}$ can enable easy and accurate measurement of the composition and film thickness of an SiGeC layer during the manufacturing process of a semiconductor device provided with an SiGeC layer. Thus, product control can be appropriately conducted, and degradation of the SiGeC layer characteristics can be prevented and the production yield can be improved. The monitor area $R_{mn}$ can also be used to analyze defects after semiconductor chips are manufactured.

In the present embodiment, the method for manufacturing a semiconductor device provided with the Si/SiGeC layer 111 is described. However, the composition and film thickness of the SiGeC layer can be measured in the same manner as described above even if an SiGe/SiGeC layer is provided instead of the Si/SiGeC layer.

INDUSTRIAL APPLICABILITY

As described above, the present invention can provide a method for measuring semiconductor constituent element content, by which the constituent element content of an SiGeC layer can be easily and accurately measured. Further, the present invention can provide a method for manufacturing a semiconductor device which can enhance the production yield thereof.

What is claimed is:

1. A method for measuring semiconductor constituent element content comprising the step of obtaining a C content of a SiGeC layer based on a film thickness of the SiGeC layer formed on a semiconductor substrate, the film thickness being obtained by evaluation using spectroscopic ellipsometry, and a measured infrared absorption spectrum of the SiGeC layer.

2. The method for measuring semiconductor constituting element content according to claim 1, wherein the step of obtaining the C content of the SiGeC layer comprises the steps of:
    calculating unit integrated intensity obtained by normalizing integrated intensity at a peak portion of the infrared absorption spectrum by the film thickness of the SiGeC layer; and
    extracting the C content corresponding to the calculated unit integrated intensity.

3. The method for measuring semiconductor constituent element content according to claim 2, wherein the step of extracting the C content corresponding to the unit integrated intensity is carried out based on linear correlation showing the relation between the measured unit integrated intensity and the C content.

4. The method for measuring semiconductor constituent element content according to claim 1, wherein obtaining the film thickness of the SiGeC layer comprises the step of using a reference model for a SiGe layer.

5. The method for measuring semiconductor constituent element content according to claim 1 further comprising the steps of:
    obtaining an apparent Ge content of the SiGeC layer by evaluation using spectroscopic ellipsometry; and
    obtaining an actual Ge content of the SiGeC layer based on the apparent Ge content and the C content.

6. The method for measuring semiconductor constituent element content according to claim 5, wherein the step of obtaining the actual Ge content of the SiGeC layer is carried out based on linear correlation showing the relation between the measured apparent Ge content and the C content.

7. The method for measuring semiconductor constituent element content according to claim 5, wherein the step of obtaining the actual Ge content of the SiGeC layer comprises the steps of:
    obtaining a plurality of correlated straight lines using a parameter of the actual Ge content, which show the relation between the apparent Ge content and the C content;
    calculating slope of each correlated straight line;
    approximating to a curve the relation between the actual Ge content and the slope of the each correlated straight line; and
    calculating the actual Ge content based on the apparent Ge content and the C content using the approximated curve.

8. A method for manufacturing a semiconductor device comprising the steps of:
    establishing a chip area and a monitor area on a semiconductor substrate;
    forming a SiGeC layer in the chip area and the monitor area;
    obtaining a film thickness and an apparent Ge content of the SiGeC layer formed in the monitor area by evaluation using spectroscopic ellipsometry;
    obtaining C content of the SiGeC layer based on the film thickness of the SiGeC layer and the measured infrared absorption spectrum of the SiGeC layer;
    obtaining an actual Ge content of the SiGeC layer based on the apparent Ge content and the C content; and
    feeding back the evaluation data of the obtained C content, actual Ge content and film thickness of the SiGeC layer to growth conditions for the SiGeC layer.

9. The method for manufacturing a semiconductor device according to claim 8, wherein the step of feeding back the evaluation data to the growth conditions of the SiGeC layer comprises the step of correcting the growth conditions of the SiGeC layer when any predetermined deviation is found by comparing the C content, the actual Ge content, and the film thickness of the SiGeC layer with a preset reference value for each.

10. The method for manufacturing a semiconductor device according to claim 8, wherein the chip area and the monitor area are individually related to any of a plurality of areas that are formed by being divided after the semiconductor device is manufactured.

11. The method for manufacturing a semiconductor device according to claim 8, wherein the chip area and the monitor area coexist with any of a plurality of areas that are formed by being divided after the semiconductor device is manufactured.

12. The method for manufacturing a semiconductor device according to claim 8, wherein the monitor areas are provided in two or more divided areas.

13. The method for manufacturing a semiconductor device according to claim 8, wherein the step of forming the SiGeC layer in the chip area and the monitor area comprises the step of growing the SiGeC layer on the semiconductor substrate and then forming a Si/SiGeC layer by growing an Si layer on the SiGeC layer.

14. The method for manufacturing a semiconductor device according to claim 13, further comprising the step of forming a hetero junction bipolar transistor in the chip area.

15. The method for manufacturing a semiconductor device according to claim 8, wherein the step of forming the SiGeC layer in the chip area and the monitor area comprises the step of growing the SiGeC layer on the semiconductor substrate and then forming an SiGe/SiGeC layer by growing an SiGe layer on the SiGeC layer.

16. The method for manufacturing a semiconductor device according to claim 15, further comprising the step of forming a hetero junction bipolar transistor in the chip area.

* * * * *

UNITED STATES PATENT AND TRADEMARK OFFICE
CERTIFICATE OF CORRECTION

PATENT NO.   : 6,858,454 B1
DATED        : February 22, 2005
INVENTOR(S)  : Yoshihiko Kanzawa et al.

It is certified that error appears in the above-identified patent and that said Letters Patent is hereby corrected as shown below:

Title page,
Item [75], Inventors, change "Yoshihiko Kanzawa, Yawata (JP)" to -- Yoshihiko Kanzawa, Kyoto (JP) -- and change "Tohru Saitoh, Ibaraki (JP)" to -- Tohru Saitoh, Osaka (JP) --.

Signed and Sealed this

Twenty-fourth Day of May, 2005

JON W. DUDAS
*Director of the United States Patent and Trademark Office*